United States Patent [19]

Greco

[11] Patent Number: 5,057,089

[45] Date of Patent: Oct. 15, 1991

[54] SYRINGE NEEDLE GUARD

[76] Inventor: Robert M. Greco, 2 Pear St., Schuylkill Haven, Pa. 17972

[21] Appl. No.: 592,907

[22] Filed: Oct. 4, 1990

[51] Int. Cl.$^5$ .............................................. A61M 5/32
[52] U.S. Cl. ..................................... 604/198; 604/263
[58] Field of Search ................ 604/198, 263, 187, 192

[56] References Cited

U.S. PATENT DOCUMENTS

| | | | |
|---|---|---|---|
| 4,695,274 | 9/1987 | Fox | 604/198 |
| 4,927,018 | 2/1990 | Yang et al. | 604/198 X |
| 4,961,730 | 10/1990 | Poncy | 604/198 |

FOREIGN PATENT DOCUMENTS 350186  1/1990  European Pat. Off. ............ 604/198

Primary Examiner—John D. Yasko
Attorney, Agent, or Firm—Richard C. Litman

[57] ABSTRACT

A syringe needle guard is adaptable to the common syringe to provide for protection against accidental needle sticks. The adaptable needle guard provides a safety sleeve for use over any standard syringe without any modification to the syringe itself. A sleeve arm is provided on the sleeve and projects upward to lie substantially at the same level as the syringe's plunger. This allows the arm to be pushed down to cover the needle with only one hand. The sleeve temporarily locks in place to secure the sleeve in either an extended protective position or in a withdrawn needle exposing position. In an alternate embodiment of the present invention the syringe can be modified at the time of manufacture to contain the safety sleeve and plunger.

14 Claims, 2 Drawing Sheets

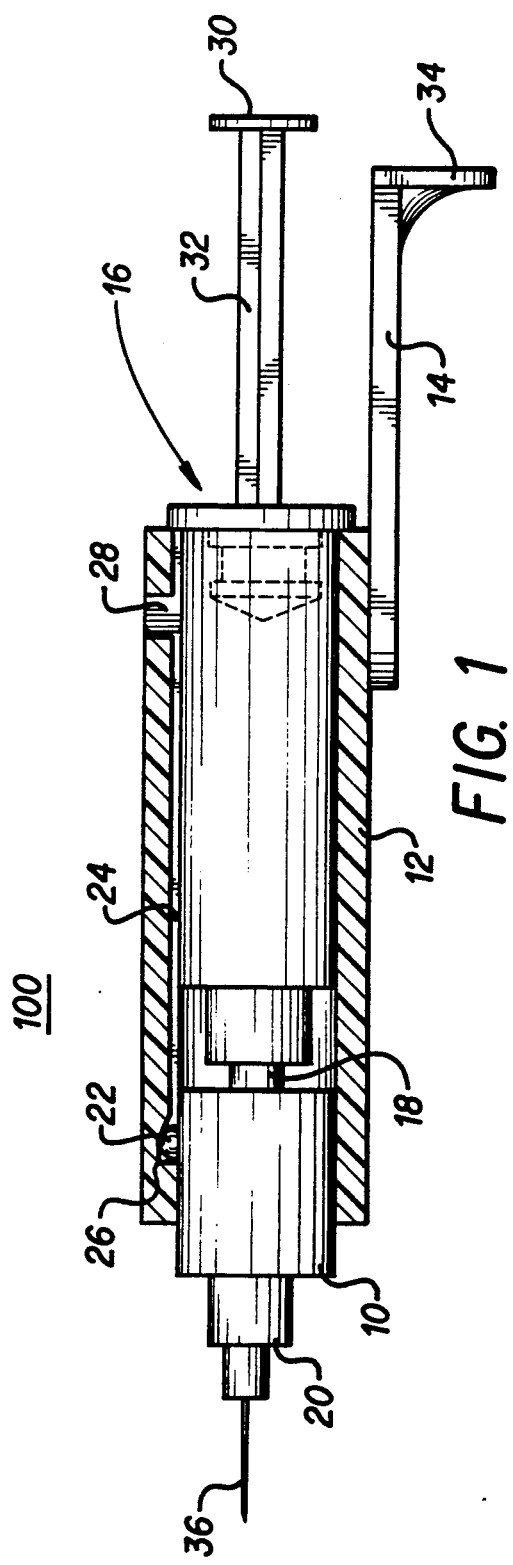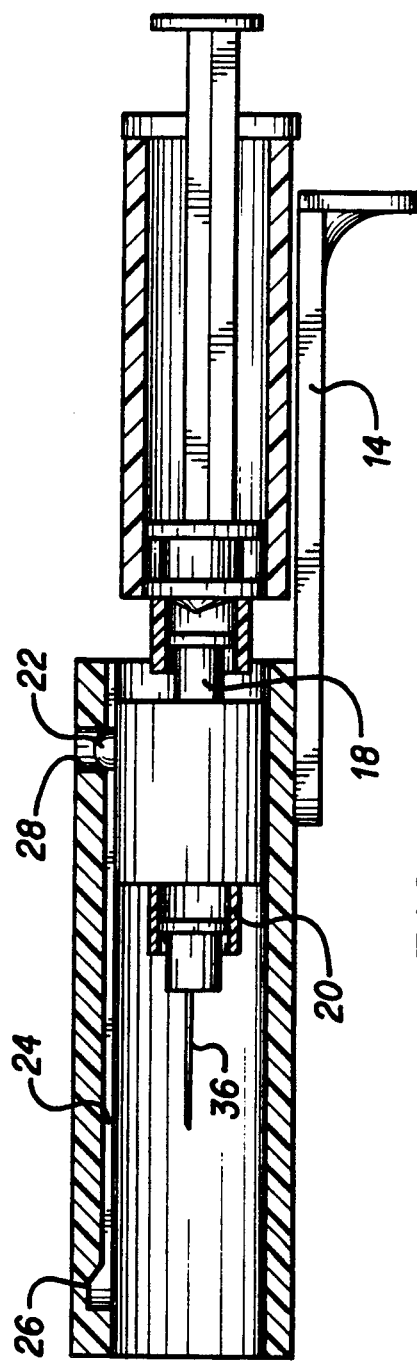

SYRINGE NEEDLE GUARD

FIELD OF INVENTION

This invention relates generally to needle guards for syringes, and more particularly to an improved syringe needle guard, which is adaptable to fit over standard unmodified syringes, and enables the user to protect and shield the needle by using only one hand.

BACKGROUND OF THE INVENTION

Various apparatuses, such as hypodermic syringes and intravenous needles are utilized for injecting a substance into humans and animals. Apparatuses of this type typically comprise a body adapted to have the substance to be injected passed therethrough and a needle mounted on the body. The substance to be injected can be forced through the needle in various ways, such as by a plunger carried by the body or by external means, such as a pump or gravitational flow.

Apparatuses of this type are typically disposable and are discarded after use. One problem presented by the disposal of these apparatuses is in shielding the sharp end of the needle so that those handling it will not be accidentally stuck. This is particularly important because, following the injection, the needle may be contaminated and spread blood-transmitted diseases, such as hepatitis or acquired immune deficiency syndrome (AIDS). AIDS is presently one of the most dangerous diseases to contract, because it causes a breakdown of the immune system that renders individuals vulnerable to a variety of serious opportunistic diseases.

The need has arisen for a needle guard for a hypodermic syringe which can be manipulated by using only one hand and which can be installed on any common syringe, especially those of the disposable type. It follows that any syringe needle guard with these abilities will present a unique advancement in the art.

DESCRIPTION OF THE RELATED ART

The broad concept of providing a protective sheath or sleeve around needles is generally known. Prior art mechanisms have generally attached the sleeve to the syringe body while allowing for axial movement of the sleeve. U.S. Pat. No. 4,723,943 issued to Spencer discloses a syringe with a body and a needle at one end and an injection plunger movable into the body at the opposite end. A sheath is positioned over the syringe body with a longitudinal groove that engages a guide lug fixed on the syringe body near the needle end. A disadvantage to this device is that the protective sleeve cannot be used on a normal unmodified syringe, typically of the disposable type. A further disadvantage is that two hands are required to place the sleeve in the protective position.

U.S. Pat. No. 4,767,413 issued to Haber et al. discloses a disposable dental syringe with a protective sleeve. Upon completing an injection, the ampule is released from the distal position and moved proximally through the cylinder, so that the distal end of the needle is automatically retracted within the cylinder. While this mechanism provides for one handed needle shielding, it does not provide any means to be adaptable to a normal unmodified syringe.

U.S. Pat. No. 4,573,976 issued to Sampson et al. discloses a syringe with a needle guard which is mounted on the syringe cylinder. When the needle guard is extended it obstructs access to the point of the needle, and when retracted it does not materially obstruct access to the point of the needle. While this device provides anti-stick protection, no means are provided for one hand actuation of the needle guard, use of the device on an unmodified, normal syringe, or means to separate the needle from the syringe body while shielding the needle to protect against needle sticks.

None of the above listed patents are seen to disclose the specific arrangement of concepts disclosed by the present invention.

SUMMARY OF THE INVENTION

By the present invention, an improved syringe needle guard which can be adapted to any common syringe is provided. The syringe needle guard is more appropriately called an adapter, in that it can be adapted to fit most common disposable and non-disposable syringes. In many medical applications it is desirable to use needles and syringes of different sizes. An adapter, preferably utilizing Luer-Lok type connections, is required as an intermediary between the needle and syringe.

The present invention is particularly advantageous with arterial blood gas syringes. An arterial blood gas syringe is used to withdraw blood from a patient. After the blood is withdrawn, the needle is discarded and the blood is stored in the syringe cylinder. The contents of the syringe cylinder can then be tested. The present invention allows the needle to be discarded while covered by a protective sleeve. This prevents the occurrence of an accidental needle stick after the blood withdrawal.

In the present invention the adapter is modified to allow a protective sleeve to slide over it. A nub or ridge is placed on the adapter and slides within a groove in the protective sleeve. Alternatively, the nub or ridge could be placed on the inside of the protective sleeve while the groove or channel can be on the adapter or syringe body. A sleeve arm can be present on the protective sleeve to facilitate manipulation of the sleeve. In operation of the device the protective sleeve is kept in the retracted position, substantially covering the syringe body. A temporary friction lock retains the protective sleeve in this position. After an injection or aspiration is made the sleeve arm is pushed down, thereby axially moving the protective sleeve along the syringe until the needle is covered. When the protective sleeve is in the extended position, a higher resistance friction lock maintains the protective sleeve over the needle. A major advantage to this type of sleeve and arm type mechanism is that the needle can be covered and uncovered with only one hand. This allows the other hand to be free to apply pressure to the artery or vein of a patient.

Given the problems and challenges of proper syringe and needle manipulation and disposal, it is an object of the present invention to provide a syringe with an integral sheath to facilitate user protection from inadvertent needle sticks.

Another object of the present invention is to provide a syringe needle guard that can easily be manipulated by using only one hand.

An additional object of the present invention is to provide a syringe needle guard that can be adapted to fit a large number of standard or modified disposable and non-disposable needles and syringes.

A further object of the present invention is to provide a syringe needle guard that includes an arm attached to the needle guard and which lies substantially near the injection plunger of the syringe.

Yet another object of the present invention is to provide a syringe needle guard which can be temporarily locked in either the retracted or extended position, while still being able to be manipulated by one hand.

A still further object of the present invention is to provide a syringe needle guard which allows the user to remove and discard the needle, protective sleeve and adapter together, while separately removing the syringe cylinder to test the withdrawn blood sample.

With these and other objects in view which will more readily appear as the nature of the invention is better understood, the invention consists in the novel combination and assembly of parts hereinafter more fully described, illustrated and claimed with reference being made to the attached drawings.

BRIEF DESCRIPTION OF THE DRAWINGS

FIG. 1 is a side elevational view in section illustrating the principle components of the present invention.

FIG. 2 is a side elevational view, partly in section.

Similar reference characters designate corresponding parts throughout the several figures of the drawings.

DESCRIPTION OF THE PREFERRED EMBODIMENT

Figure 3:
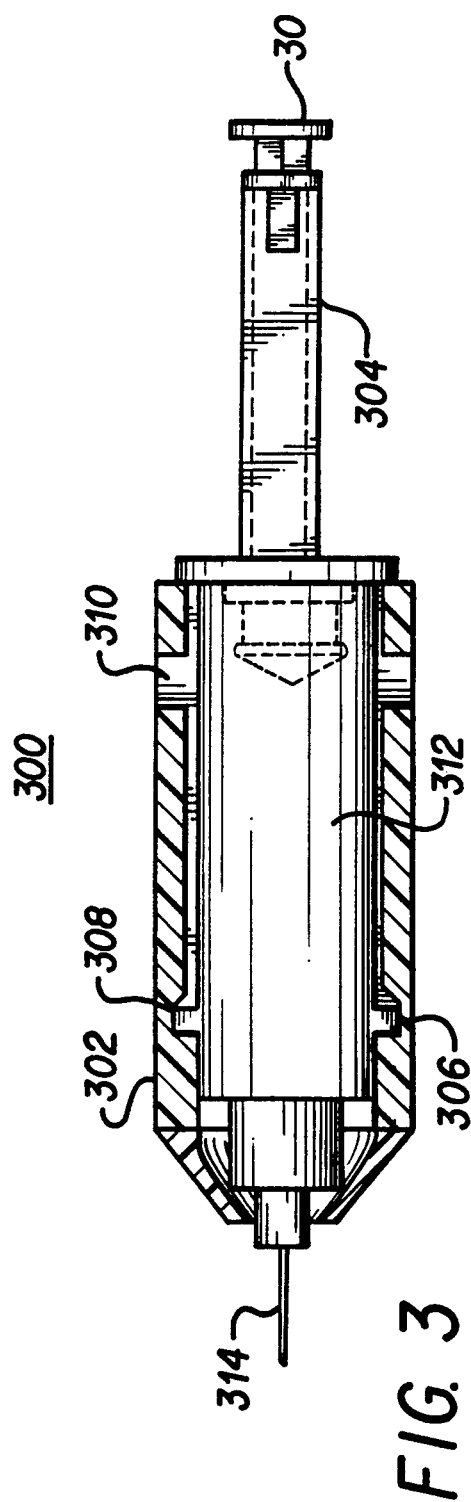
FIG. 3 is a side elevational view, partly in section, of an alternate embodiment of the present invention.

Referring now to the drawings, particularly FIG. 1, the present invention will be understood to relate to an improved syringe needle guard which can be adapted to fit a variety of syringe bodies and needles. The needle guard 100 includes adapter 10, protective sleeve 12 and sleeve arm 14. The needle guard 100 can be retrofitted over a normal syringe 16. The adapter 10 includes connectors for fluid connection to the syringe and needle. There are typically a male end connector 18 and female end connector 20, preferably but not limited to the Leur-Lok type. The adapter 10 provides for free flow of fluid from the male end 18 to the female end 20. A locking nub 22 is also attached to the adapter 10. The locking nub 22 fits into longitudinal channel 24 in protective sleeve 12.

Two friction locks are present in the protective sleeve 12. Lock 26 is a low friction temporary lock to keep the protective sleeve 12 in a withdrawn, needle exposing position. Lock 28 is a higher friction lock, more resistant to movement, to keep the protective sleeve 12 in an extended, needle covering position. The sleeve arm 14 is formed integrally with the protective sleeve 12 and is used to position the protective sleeve 12 in either the needle exposing position, as shown in FIG. 1, or in the needle covering position, as shown in FIG. 2. The thumb rest 30 of the injection plunger 32 can be at approximately the same level as the thumb rest 34 of sleeve arm 14. This allows easy access to both of the thumb rests 30 and 34 with the hand that is holding the syringe 16 and needle guard 100.

Alternative structures for the locking mechanism could place the locking nubs or circumferential ridge on the inside of the protective sleeve, while the groove or channel could be placed on the adapter 10 or syringe body. A nub on the inside of the protective sleeve could fit into axially extending ridges on the adapter or syringe body. The locking mechanisms can utilize multiple locks with equal coefficients of friction, or, multiple locks with unequal coefficients of friction.

In FIG. 3 an alternate embodiment of the present invention is shown. This embodiment illustrates a syringe modified at the time of manufacture. Syringe 300 includes protective sleeve 302 with sleeve arm 304. In this embodiment a circumferential locking ring 306 can replace the locking nub 22. Locks 308 and 310 function identically to locks 26 and 28 respectively. When the sleeve arm 304 is pushed towards the distal end of syringe 312, the locking ring 306 will disengage from lock 308 and the protective sleeve 302 will move axially along syringe 312 to cover needle 314. The protective sleeve will entirely cover needle 314 when locking ring 306 engages with lock 310.

Figure 4:
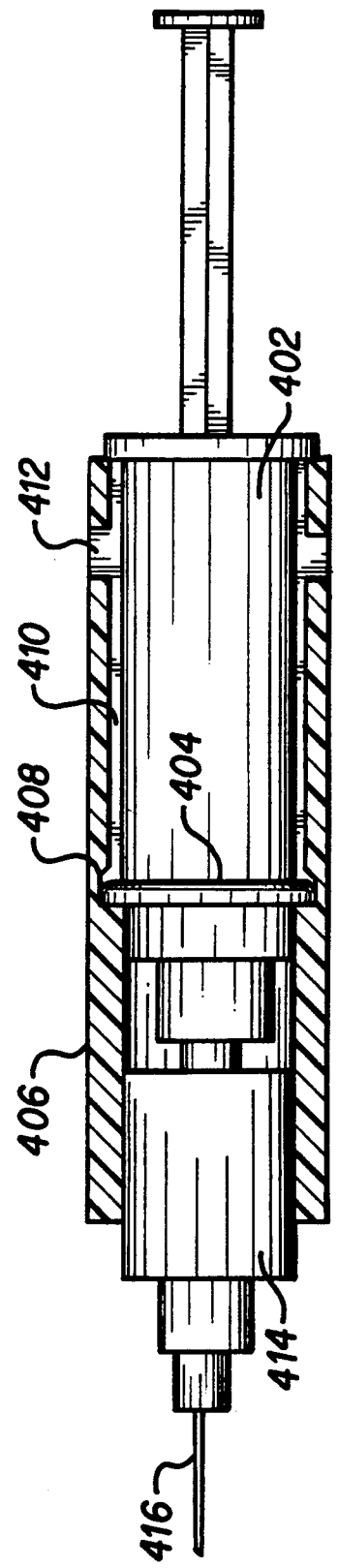
FIG. 4 is a side elevational view, partly in section, of a further embodiment of the present invention.

In FIG. 4 a similar embodiment of the present invention as in FIG. 3 is shown. In this embodiment the syringe and needle guard are formed integrally at the time of manufacture. Syringe 402 contains a circumferential locking ring 404 about its outer diameter. The protective sleeve 406 contains lock 408, channel 410 and lock 412. An adapter 414 is shown attached to syringe 402 and needle 416. The protective sleeve 406 is of a longer length than the protective sleeve 302 to accommodate the attachment of adapter 414.

In operation of the device 100, referring to FIGS. 1 and 2, the device 100 is particularly useful in arterial blood gas syringes. Prior to inserting the needle 36 into a patient, the protective sleeve 12 can be covering the needle 36 as shown in FIG. 2. This will protect against accidental needle sticks to the patient and/or medical staff. To make the injection or aspiration, the sleeve arm 14 is pulled back towards the injection plunger 32 with the thumb of the hand that is holding the syringe 16. The needle 36 will now be exposed and the injection or aspiration can be made. After the injection or aspiration is accomplished the needle is removed from the patient, and pressure must be applied to the injection site. The person making the injection must hold the syringe with one hand and apply pressure with the other. With the sleeve arm of the present invention the person who made the injection can use one hand to push the protective sleeve 12 over needle 36. By these means the needle 36 can always be protected or covered by protective sleeve 12 immediately prior and subsequent to injection by the use of the same hand which is holding the syringe 16.

It is to be understood that the present invention is not limited to the embodiments described above, but encompasses any and all embodiments within the scope of the following claims.

I claim:

1. For use with a syringe of the type having a syringe body internally accepting an injection plunger to define a fluid containing space communicating with a syringe needle for injecting fluid, said syringe needle joined to said syringe body by fluid-tight connectors, said connectors including a first body-type connector axially disposed on said syringe body distal said plunger and a first needle-type connector axially disposed on said syringe needle for mating with said first body-type connector, said syringe body and said syringe needle cylindrical and coaxial, said syringe body having an outer body diameter, a needle guard comprising:
a protective hollow sleeve axially movable along said syringe body, said sleeve including a distal end and a proximal end, said sleeve having an internal sleeve diameter greater than said external body diameter for accepting said syringe body therein, said proximal end open to accept therethrough said syringe body so that said injection plunger extends from said proximal end;

an adapter disposed within said sleeve and slidable within said sleeve, said adapter including a cylindrical outer adapter surface having an outer adapter diameter less than said internal sleeve diameter and generally equal to said external body diameter.

said adapter including a second needle-type connector axially disposed and adapted for fluid connection to said first body-type connector of said syringe body to join said syringe body and said adapter into a slide unit, a second body-type connector axially disposed and adapted for fluid connection to said first needle-type connector of said syringe needle, and a fluid passage between said second body-type connector and said second needle-type connector; and a distal lock adjacent said distal end of said sleeve, and a proximal lock adjacent said proximal end of said sleeve, said distal lock adapted to hold said slide unit within said sleeve at a distal position adjacent said distal end, and said proximal lock adapted to hold said slide unit within said sleeve at a proximal position adjacent said proximal end;

said sleeve adapted in length to substantially cover said syringe needle when said syringe needle is joined to said slide unit and said slide unit is in said proximal position, and to uncover said syringe needle when said syringe needle is joined to said slide unit and said slide unit is in said distal position.

2. For use with a syringe of the type having a syringe body internally accepting an injection plunger to define a fluid containing space communicating with a syringe needle for injecting fluid, a needle guard comprising:

a protective hollow sleeve axially movable along said syringe body, said sleeve including a distal end and a proximal end, said proximal end adapted to accept therethrough said syringe body so that said injection plunger extends from said proximal end;

an adapter disposed within said sleeve and slidable within said sleeve, said adapter including a body connector adapted for fluid connection to said syringe body, a needle connector adapted for fluid connection to said syringe needle, and a fluid passage between said body connector and said needle connector;

a distal lock adjacent said distal end of said sleeve, and a proximal lock adjacent said proximal end of said sleeve, said distal lock adapted to hold said adapter within said sleeve at a distal position adjacent said distal end, and said proximal lock adapted to hold said adapter within said sleeve at a proximal position adjacent said proximal end;

a sleeve arm mounted on to said sleeve adjacent said proximal end of said sleeve and projecting in a proximal direction parallel said injection plunger, said sleeve arm terminating distant from said sleeve in a proximal sleeve arm end; and a thumb rest fixed normally on said proximal sleeve arm end, said thumb rest lying substantially near to the proximal end of said injection plunger when said adapter is in said distal position;

said sleeve adapted in length to substantially cover said syringe needle when said syringe needle is connected to said needle connector and said adapter is in said proximal position, and to uncover said syringe needle when said syringe needle is connected to said needle connector and said adapter is in said distal position.

3. A needle guard according to claim 1 wherein said locks are friction locks.

4. For use with a syringe of the type having a syringe body internally accepting an injection plunger to define a fluid containing space communicating with a syringe needle for injecting fluid, a needle guard comprising:

a protective hollow sleeve axially movable along said syringe body, said sleeve including a distal end and a proximal end, said proximal end adapted to accept therethrough said syringe body so that said injection plunger extends from said proximal end;

an adapter disposed within said sleeve and slidable within said sleeve, said adapter including a body connector adapted for fluid connection to said syringe body, a needle connector adapted for fluid connection to said syringe needle, and a fluid passage between said body connector and said needle connector; and a distal lock adjacent said distal end of said sleeve, and a proximal lock adjacent said proximal end of said sleeve, said distal lock adapted to hold said adapter within said sleeve at a distal position adjacent said distal end, and said proximal lock adapted to hold said adapter within said sleeve at a proximal position adjacent said proximal end, the locks including a locking nub on the surface of said adapter, a longitudinal channel inside said protective sleeve, wherein said locking nub slides within said channel, a proximal detent within said channel for engaging said locking nub to lock said adapter in said proximal position, a distal detent within said channel for engaging said locking nub to lock said adapter in said distal position, said distal detent and said proximal detent adapted to require longitudinal forces on said locking nub parallel to the length of said sleeve for dislodging said locking nub from the detents, said sleeve adapted in length to substantially cover said syringe needle when said syringe needle is connected to said needle connector and said adapter is in said proximal position, and to uncover said syringe needle when said syringe needle is connected to said needle connector and said adapter is in said distal position.

5. A needle guard according to claim 4 wherein said distal lock requires less force for dislodging than does said proximal lock.

6. A needle guard according to claim 1 wherein said locks further comprise:

means to prevent relative axial rotation of said sleeve and said adapter;

a locking detent mounted on to said adapter;

a proximal nub within said sleeve for engaging said locking detent to lock said adapter in said proximal position; and a distal nub within said sleeve for engaging said locking detent to lock said adapter in said distal position, said distal nub and said proximal nub adapted to require longitudinal forces on said locking detent parallel to the length of said sleeve for dislodging said locking detent from the nubs.

7. A needle guard according to claim 6 wherein said distal lock requires less force for dislodging than does said proximal lock.

8. A needle guard according to claim 1 wherein said locks further comprise:

a circumferential locking ridge mounted on to said adapter;

a circumferential proximal detent groove within said sleeve for engaging said locking ridge to lock said adapter in said proximal position;

a circumferential distal detent groove within said sleeve for engaging said locking ridge to lock said adapter in said distal position;

said distal groove and said proximal groove adapted to require longitudinal forces on said locking ridge parallel to the length of said sleeve for dislodging said locking ridge from the grooves.

9. A needle guard according to claim 8 wherein said distal lock requires less force for dislodging than does said proximal lock.

10. A needle guard according to claim 1 wherein said distal lock requires less force for dislodging than does said proximal lock.

11. A needle guard according to claim 1 including a sleeve arm mounted on to said protective sleeve adjacent said proximal end of said sleeve and projecting in a proximal direction generally parallel said injection plunger, said sleeve arm terminating distant from said sleeve in a proximal sleeve arm end.

12. A needle guard according to claim 11 including a thumb rest fixed normally on said proximal sleeve arm end.

13. For use with a syringe of the type having a syringe body internally accepting an injection plunger to define a fluid containing space communicating with a syringe needle for injecting fluid, said syringe needle joined to said syringe body by fluid-tight mating connectors axially disposed, said syringe body and said syringe needle cylindrical and coaxial, said syringe body having an outer body diameter, a needle guard comprising:

a protective hollow sleeve axially movable along said syringe body, said sleeve including a distal end and a proximal end, said sleeve having an internal sleeve diameter greater than said external body diameter for accepting said syringe body therein, said proximal end open to accept therethrough said syringe body so that said injection plunger extends from said proximal end;

a distal lock adjacent said distal end of said sleeve, and a proximal lock adjacent said proximal end of said sleeve, said distal lock adapted to hold said syringe body within said sleeve at a distal position adjacent said distal end, and said proximal lock adapted to hold said syringe body within said sleeve at a proximal position adjacent said proximal end; and a sleeve arm mounted on to said sleeve adjacent said proximal end of said sleeve and projecting in a proximal direction parallel said injection plunger, said sleeve arm terminating distant from said sleeve in a proximal sleeve arm end;

said sleeve adapted in length to substantially cover said syringe needle when said syringe needle is joined to said syringe body and said syringe body is in said proximal position, and to uncover said syringe needle when said syringe needle is joined to said syringe body and said syringe body is in said distal position.

14. A needle guard according to claim 12 including a thumb rest fixed normally on said proximal sleeve arm end, said thumb rest lying substantially near to the proximal end of said injection plunger when said adapter is in said distal position.

* * * * *